United States Patent [19]

Dunn et al.

[11] Patent Number: 5,734,011
[45] Date of Patent: Mar. 31, 1998

[54] LIGAND PRECURSORS FOR INCORPORATION INTO PEPTIDES

[75] Inventors: T. Jeffrey Dunn, Cedar Hill; Ananthachari Srinivasan, St. Charles, both of Mo.

[73] Assignee: Mallinckrodt Medical, Inc., St. Louis, Mo.

[21] Appl. No.: 469,028

[22] Filed: Jun. 6, 1995

Related U.S. Application Data

[62] Division of Ser. No. 382,839, Feb. 3, 1995, abandoned, which is a continuation of Ser. No. 62,099, May 14, 1993, abandoned.

[51] Int. Cl.$^6$ ........................................ A61K 38/03
[52] U.S. Cl. .................. 530/300; 530/326; 530/327; 530/328; 530/329; 530/330; 530/335; 530/337; 560/155; 560/553
[58] Field of Search ........................ 530/300, 335, 530/337, 326–330; 560/155; 562/553

[56] References Cited

U.S. PATENT DOCUMENTS 4,476,050  10/1984  Kitaura et al. ................. 260/112.5
4,868,326   9/1989  Bouchaudon et al. ............ 560/159

OTHER PUBLICATIONS

Caplus Abstract No. 1976:59978(Tsuji et al.).
Chemical Abstract No. 111: 23232(b) to Bouchaudon et al.
Rosowsky et al., J. Org. Chem. vol. 54 No. 23 (1989) pp. 5551–5557.
Obeidi et al., Int. J. Pept. Prot. Res. vol. 35(1990) 215–218.

*Primary Examiner*—Cecilia J. Tsang
*Assistant Examiner*—Bennett Celsa

[57] ABSTRACT

Compositions and methods of incorporating ligand precursors and ligands at any location within a peptide during peptide synthesis are disclosed. Derivatives of 2,4,5-triaminopentanoic acid and γ-aminoglutamic acid are selectively incorporated into the peptide during solid phase or liquid phase synthesis, depending upon the choice of protecting groups. Ligand synthesis may then be completed at a later time to produce $N_3S$, $N_2S_2$, and EDTA type chelating agents.

2 Claims, No Drawings

LIGAND PRECURSORS FOR INCORPORATION INTO PEPTIDES

This is a divisional of prior application Ser. No. 08/382,839 filed on Feb. 3, 1995, now abandoned, which is a continuation of application Ser. No. 08/062,099 filed on May 14, 1993, of T. Jeffrey Dunn and Ananthachari Srinivasan for LIGAND PRECURSORS FOR INCORPORATING INTO PEPTIDES, now abandoned.

BACKGROUND

1. Field of the Invention

This invention relates generally to bifunctional chelating agents. More particularly, the present invention relates to ligand precursors, such as derivatives of 2,4,5-triaminopentanoic acid and γ-aminoglutamic acid, which are selectively incorporated at any desired location during peptide synthesis.

2. Technology Background

Scintigraphic imaging and similar radiographic techniques for visualizing tissues in vivo are finding ever-increasing application in biological and medical research and in diagnostic and therapeutic procedures. Generally, scintigraphic procedures involve the preparation of radioactive agents which upon introduction to a biological subject, become localized in the specific organ, tissue or skeletal structure of choice. When so localized, traces, plots or scintiphotos depicting the in vivo distribution of radiographic material can be made by various radiation detectors, e.g., traversing scanners and scintillation cameras. The distribution and corresponding relative intensity of the detected radioactive material not only indicates the space occupied by the targeted tissue, but also indicates a presence of receptors, antigens, aberrations, pathological conditions, and the like.

In general, depending on the type of radionuclide and the target organ or tissue of interest, the compositions comprise a radionuclide, a carrier agent such as a biologically active protein or peptide designed to target the specific organ or tissue site, various auxiliary agents which affix the radionuclide to the carrier such as bifunctional chelating agents, water or other delivery vehicles suitable for injection into, or aspiration by, the patient, such as physiological buffers, salts, and the like. The auxiliary agent attaches or complexes the radionuclide to the peptide carrier agent, which permits the radionuclide to localize where the carrier agent concentrates in the biological subject.

Recently, EDTA-like compounds bearing side chains containing amino and carboxylic groups have been reported as bifunctional chelating agents. Warshawsky and coworkers reported the synthesis of compounds 1 (*J. Chem. Soc., Chem. Comm.*, 1133 (1985) and *Synthesis*, 825 (1989)) and 2 (*J. Chem. Soc., Perkin Trans. I.*, 59 (1984)), shown below, as bifunctional chelating agents. Arya and Gariépy (*Bioconjugate Chem.*, 2, 323 (1991)) synthesized compound 3 for incorporation into the amino terminal during solid phase peptide synthesis.

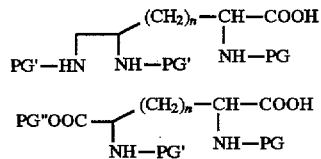

| Compound | n | R | R' |
|---|---|---|---|
| 1 | 2 | H | COOH |
| 2 | 2 | H | NH—R |
| 3 | 0 | tBu | COOH |

In the above cases, the carboxylic acid or the derivatized amine is used for covalent linkage to proteins and peptides. Such an approach is limited to incorporation of the EDTA like compounds either at the amino or carboxyl terminal of the peptide.

Often the amino or carboxyl terminal of the peptide is biologically active, such that conjugating a ligand to the terminal end of the peptide destroys the peptide's bioactivity. If the peptide's bioactivity is destroyed, then the peptide subsequently labeled with a radioisotope will have little value in diagnostic or therapeutic application.

It will be appreciated that there is a need in the art for compositions and methods of incorporating ligand precursors and ligands capable of forming metal complexes at any location within the peptide. It would also be a significant advancement in the art to permit radiolabeling of peptides without destroying the peptide's bioactivity.

Such compositions and methods are disclosed and claimed herein.

BRIEF SUMMARY OF THE INVENTION

The present invention relates to compositions and methods of incorporating ligand precursors and ligands at any location within a peptide without affecting the bioactivity of the peptide. According to the present invention, derivatives of 2,4,5-triaminopentanoic acid and γ-aminoglutamic acid, below, are selectively incorporated into the peptide during solid phase or liquid phase synthesis depending upon the choice of protecting groups.

$$\text{PG'—HN} \overset{(CH_2)_n—CH—COOH}{\underset{NH—PG'}{\Big|}} \overset{|}{NH—PG}$$

$$\text{PG''OOC} \overset{(CH_2)_n—CH—COOH}{\underset{NH—PG'}{\Big|}} \overset{|}{NH—PG}$$

The ligand synthesis may then be completed at a later time to produce $N_3S$, $N_2S_2$, and EDTA type chelating agents. Ligands may be synthesized having complex formation kinetics tailored to specific radionuclides. For example, $N_3S$ ligands may be useful for complexing Tc, Re, and Cu; $N_2S_2$ ligands may be useful for complexing Tc, Re, and Cu; and EDTA-type ligands may be useful for complexing In, Ga, and Y. It is also possible to synthesize ligands such that the radionuclide prefers the ligand coordination site (i.e., has favorable complex formation kinetics) as opposed to other coordination sites along the peptide.

It is therefore an object of the present invention to provide compositions and methods of incorporating ligand precursors and ligands at any location within a peptide during either solid phase or liquid phase peptide synthesis.

DETAILED DISCLOSURE OF THE INVENTION

The key compounds 4 and 5, shown below, with appropriate orthogonal protecting groups (PG, PG', or PG") can be incorporated in peptides by either solid phase or solution phase synthesis.

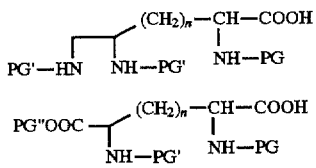

Unlike compounds 1–3 of the prior art, compounds 4 and 5 can be incorporated at any position within the peptide chain. Through the use of known protecting groups, one can position the ligand precursor at any location within the peptide and either complete the peptide synthesis or complete the ligand synthesis. For example, N-α-t-Boc (tert-butyloxycarbonyl) amino acids with the distal vicinal amino groups protected with Fmoc (9-fluorenylmethoxy-carbonyl) groups will allow one to incorporate either an EDTA moiety or $N_2S_2$ at any location within the peptide.

Compound 4 is a versatile intermediate for incorporation of EDTA moiety either by liquid phase or solid phase method.

Solid phase. The use of compound 4 in solid phase synthesis of peptides containing $N_2S_2$ or EDTA ligand systems is illustrated below:

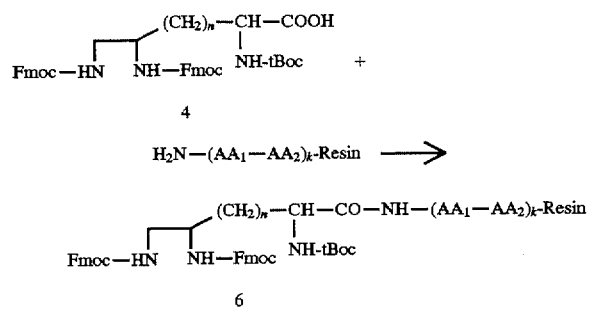

Where $(AA_1—AA_2)_k$ is a peptide chain of length k ranging from 0 to 20, and preferably k is less than 15. Once compound 4 is incorporated into the peptide to produce compound 6, two options are available. Either the ligand synthesis can be completed, followed by continued peptide synthesis or the peptide synthesis can be completed, followed by ligand synthesis. For example, the Fmoc groups can be removed and protected mercaptoacetic acid derivatives (e.g., S-protected as trichloroethoxycarbonyl, S-Fmoc) are condensed followed by removal of t-Boc ("tert-butyloxycarbonyl") groups to form a $N_2S_2$ ligand. The peptide elongation can then be continued.

Alternatively, the t-Boc group may be removed with trifluoroacetic acid ("TFA") and the peptide synthesis continued. Prior to removal of the peptide from the resin, the Fmoc groups are removed for incorporating the mercaptoacetyl groups. Choice of protecting groups on the sulfur depends on whether a disulfide or S-acyl is needed. A combination of S-Tcam ("trimethylacetamidomethyl") and S-acyl groups can be used to build a disulfide and a $N_2S_2$ system. Suitable protecting groups include known alkyl, aryl, acyl (preferably alkanoyl or benzoyl), or thioacyl group having from 1 to about 7 carbons; or an organothio group having from 1 to about 10 carbons.

The sulfur protecting group, when taken together with the sulfur atom to be protected, may also be a hemithioacetal group. Suitable examples include, but are not limited to, those having the following formulae, wherein the sulfur atom is the sulfur atom of the chelating compound:

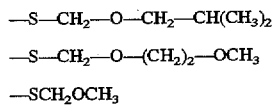

Preferred hemithioacetals and hemithioketals generally are of the following formula, wherein the sulfur atom is the sulfur atom of the chelating compound:

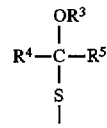

wherein $R^3$ is a lower alkyl group, preferably of from 2 to 5 carbon atoms, and $R^4$ is a lower alkyl group, preferably of from 1 to 3 carbon atoms. Alternatively, $R^3$ and $R^4$ may be taken together with the carbon atom and the oxygen atom shown in the formula to define a nonaromatic ring, preferably comprising from 3 to 7 carbon atoms in addition to the carbon and oxygen atoms shown in the formula. $R^5$ represents hydrogen or a lower alkyl group wherein the alkyl group preferably is of from 1 to 3 carbon atoms.

Examples of such preferred compounds include, but are not limited to:

Tetrahydrofuranyl   Methoxymethyl   2-methyl-tetrahydrofuranyl

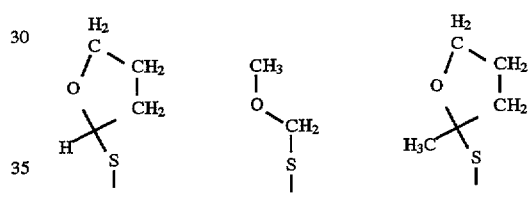

Tetrahydropyranyl   ethoxyethyl   2-methyl tetrahydropyranyl

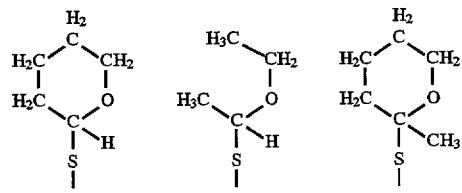

Advantages of using hemithioacetal and hemithioketal sulfur protecting groups include the fact that a separate step for removal of the sulfur-protective groups is not necessary. The protecting groups are displaced from the compound during the radiolabeling in what is believed to be metal assisted acid cleavage; i.e., the protective groups are displaced in the presence of the metal radioisotope at an acidic pH, and the radioisotope is bound by the chelating compound. The radiolabeling procedure thus is simplified, which is especially advantageous when the chelating compounds are to be radiolabeled in a hospital laboratory shortly before use. In addition, the basic pH conditions and harsh conditions associated with certain known radiolabeling procedures or procedures for removal of other sulfur protective groups are avoided. Thus, base-sensitive groups on the chelating compound survive the radiolabeling step intact. Such base labile groups include any group which may be destroyed, hydrolyzed, or other wise adversely affected by exposure to basic pH. Certain protein conjugation groups, including esters, isothiocyanates, maleimides, and other Michael acceptors, among others, are relatively base labile. Thus, a radiolabeled chelate may be prepared, and the protein conjugation group remains intact for subsequent binding of the chelate to a targeting compound (e.g., an antibody).

Alternatively, an acetamidomethyl sulfur-protecting group may be used. This group is represented by the formula:

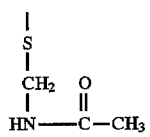

The acetamidomethyl group is displaced from the chelating compound during radiolabeling conducted at about 50° C. in a reaction mixture having a pH of about 3 to 6. The use of an acetamidomethyl group generally improves the water solubility of the chelating compound, which is desirable when the compound is to be attached to a protein or other biological targeting moiety prior to radiolabeling. Aqueous reaction mixtures are preferred for protein conjugation reactions, since organic solvents may denature or otherwise damage the protein.

In another approach, it is possible to incorporate the ligand system ($N_2S_2$ or EDTA) by prior organization. This approach is technically possible, but less desirable because the sulfur protecting groups required for the ligand are generally more labile than the protecting groups used in peptide synthesis making it difficult to preserve the fully formed ligand during peptide synthesis. The Fmoc groups from 4 are removed followed by acylation to give 8 or alkylation to give 9 prior to use in the solid phase method.

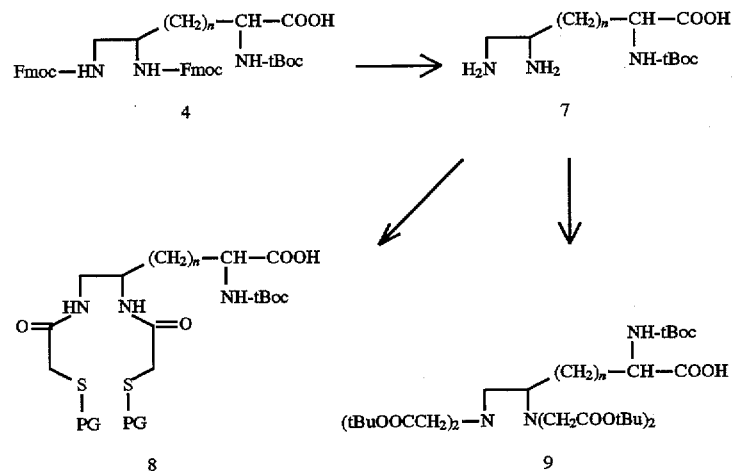

To accomplish the incorporation of $N_2S_2$, Fmoc groups are removed from 4, protected (acyl, carbamates, hemithioacetal) mercaptoacetic acids are incorporated to give 8, followed by other amino acids either by t-Boc method or Fmoc method depending on the choice of S-protecting group.

Liquid phase. A similar strategy is followed for the synthesis of peptides containing ligands by liquid phase method. The key step is the removal of N-t-Boc (from 4) group exclusively in the presence of COOtBu using p-Toluenesulfonic acid (*Tetrahedron Letters*, p. 3609 (1975)) and Fmoc amino acids are used to complete the synthesis. The application of this approach will be very useful in building ligands containing EDTA type and amide thiolate systems at any point. Application of selective N-t-Boc removal in the presence of COOtBu for solid phase and liquid phase method using alcoholic-pTsOH (para-toluene sulfonic acid) is feasible according to literature reports. E.g., J. Goodcare, R. J. Ponsford and I. Stirling, *Tetrahedron Letters*, vol. 42, p. 3609 (1975). A combination of t-Boc and Fmoc method (FAACST method, Fmoc Amino Acid Chloride Solution Technique, T. Sadat-Aalee, *Diss. Abstracts International B.*, vol. 51, p. 3850 (1990) and T. Høeg-Jensen, M. H. Jakobsen and A. Holm, *Tetrahedron Letters*, p. 6387 (1991)) will allow rapid synthesis of bioactive peptides containing chelates. Compound 10, containing the ligand is obtained using trifluoroacetic acid in a t-Boc synthesis or by sequential treatment of piperidine and trifluoroacetic acid in a combination of t-Boc-Fmoc syntheses.

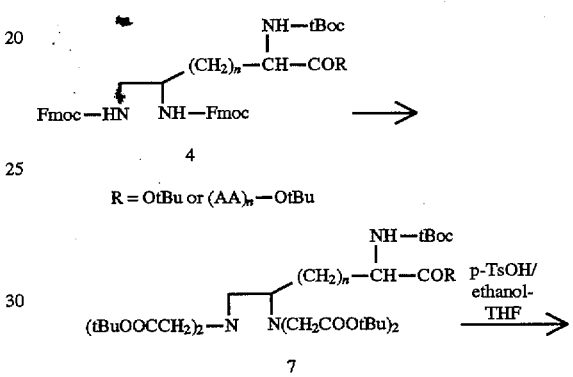

R = OtBu or (AA)$_n$—OtBu

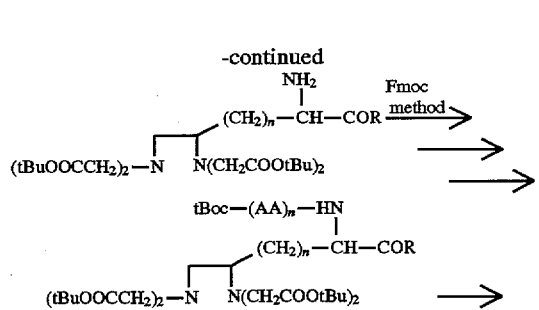

-continued

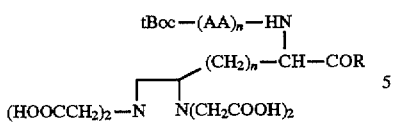
5

The preparation of key intermediate 4, can be accomplished by several routes. The Bamberger reaction (ring opening of imidazoles by acid chloride) is a currently preferred method. Method A illustrates the ring opening of t-Boc-His by 9-flourenylmethyloxycarbonyl (Fmoc) chloride to give compound 4.

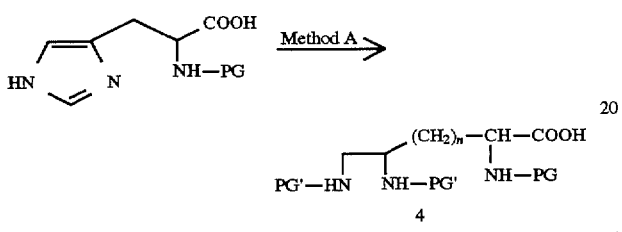
4

Method B illustrates the reaction of t-Boc-dehydroalanine with the anion of benzylidineaminoacetonitrile followed by hydrolysis, reduction and protection of amino groups to give compound 4. In the synthesis of compound 4, the acids are protected as t-butyl ester and the α-amine is protected as t-Boc.

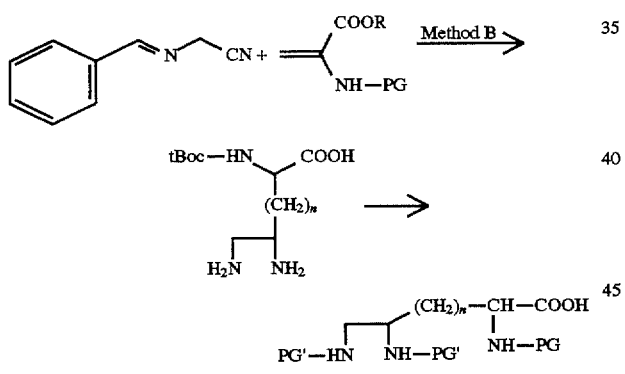
4

From orthogonally protected 5, the incorporation of $N_3S$ systems follows a similar strategy. α-Halogenation of N-t-Boc-Glu(OtBu), followed by displacement with azide, reduction (to 11) and Fmoc protection will give compound 5. It can also be prepared by Method B (see above) from N-t-Boc-DHA-t-butyl ester and benzylidene ethylglycinate. General approach to incorporation of $N_3S$ by solid phase method using 5 is given below.

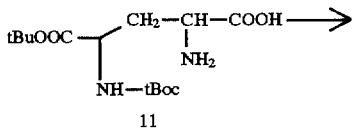
11

-continued

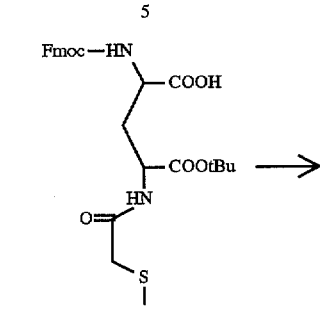
5

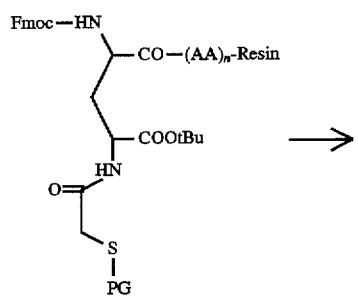

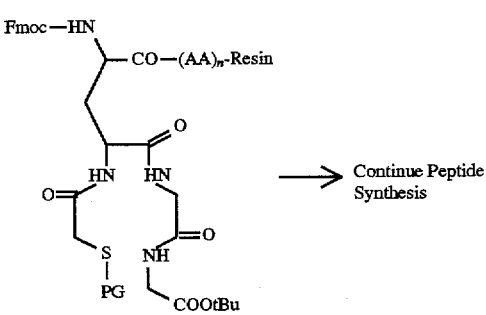

→ Continue Peptide Synthesis

Compound 11 is a useful intermediate for incorporating $N_3S$ systems by solution phase.

From the foregoing, it will be appreciated that the present invention provides compositions and methods of incorporating ligand precursors and ligands at any location within a peptide during either solid phase or liquid phase peptide synthesis.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A peptide having the following formula:

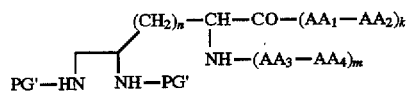

wherein PG' is an orthogonal protecting group; n is from 0 to 3; $(AA_1-AA_2)_k$ is a peptide chain of length k; $(AA_3-AA_4)_m$ is a peptide chain of length m; k and m may range from 1–15; and k and m<20.

2. A peptide having the following formula:
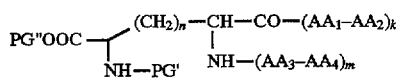
wherein PG' and PG" are orthogonal protecting groups; n is from 0 to 3; $(AA_1-AA_2)_k$ is a peptide chain of length k; $(AA_3-AA_4)_m$ is a peptide chain of length m; k and m may range from 1–15; and k and m<20.
* * * * *